US 11,607,158 B2

(12) United States Patent
Schwalenberg (10) Patent No.: US 11,607,158 B2
(45) Date of Patent: Mar. 21, 2023

(54) SENSOR AND BIOSENSOR

(71) Applicant: OSRAM OLED GmbH, Regensburg (DE)

(72) Inventor: Simon Schwalenberg, Brennberg (DE)

(73) Assignee: OSRAM OLED GMBH, Regensburg (DE)

( * ) Notice: Subject to any disclaimer, the term of this patent is extended or adjusted under 35 U.S.C. 154(b) by 630 days.

(21) Appl. No.: 16/615,889

(22) PCT Filed: May 22, 2018

(86) PCT No.: PCT/EP2018/063342
§ 371 (c)(1),
(2) Date: Nov. 22, 2019

(87) PCT Pub. No.: WO2018/215435
PCT Pub. Date: Nov. 29, 2018

(65) Prior Publication Data
US 2020/0146603 A1 May 14, 2020

(30) Foreign Application Priority Data
May 23, 2017 (DE) .................. 10 2017 111 202.2

(51) Int. Cl.
*A61B 5/1455* (2006.01)
*G01N 21/3504* (2014.01)
(Continued)

(52) U.S. Cl.
CPC ........ *A61B 5/14552* (2013.01); *A61B 5/6844* (2013.01); *G01N 21/3504* (2013.01);
(Continued)

(58) Field of Classification Search
CPC ........ A61B 5/14552; A61B 2562/0233; A61B 2562/185; A61B 5/6844; G01N 21/3504;
(Continued)

(56) References Cited

U.S. PATENT DOCUMENTS 5,130,531 A * 7/1992 Ito ..................... H01L 31/167
257/434
8,711,334 B2 4/2014 Haas et al.
(Continued)

FOREIGN PATENT DOCUMENTS

| EP | 3020332 A1 | 5/2016 |
| KR | 101456971 B1 | 11/2014 |
| WO | 2017080869 A1 | 5/2017 |

OTHER PUBLICATIONS

German Search Report based on application No. 10 2017 111 202.2 (12 pages) dated Jan. 22, 2018 (for reference purpose only).
(Continued)

*Primary Examiner* — Dominic J Bologna
(74) *Attorney, Agent, or Firm* — Viering, Jentschura & Partner mbB (57) ABSTRACT

A sensor may include a light source, a light detector, and a housing. The housing may have a first upper side and extend from the first upper side, a first cavity and a second cavity. The light detector is arranged in the first cavity. The light source is arranged in the second cavity. A strut may be arranged between the first cavity and the second cavity and is made from a material that absorbs or reflects light. A first cover may be mounted above the first cavity and comprises a deflection region and a plane of incidence. The deflection region is designed such that 80% of the light which is incident in the deflection region on the plane of incidence of the first cover from a predetermined direction and which is incident on the light detector, is directed away from the light detector based on an optical element.

19 Claims, 6 Drawing Sheets (51) Int. Cl.
  *G01N 21/47* (2006.01)
  *G01N 21/49* (2006.01)
  *A61B 5/00* (2006.01)

(52) U.S. Cl.
  CPC .......... *G01N 21/474* (2013.01); *G01N 21/49* (2013.01); *A61B 2562/0233* (2013.01); *A61B 2562/185* (2013.01); *G01N 2201/064* (2013.01)

(58) Field of Classification Search
  CPC . G01N 21/474; G01N 21/49; G01N 2201/064
  See application file for complete search history.

(56) References Cited

U.S. PATENT DOCUMENTS

| | | | |
|---|---|---|---|
| 9,506,802 B2 | 11/2016 | Chu et al. | |
| 2010/0258712 A1* | 10/2010 | Wiese | H01L 25/167 |
| | | | 257/E31.127 |
| 2011/0024627 A1* | 2/2011 | Yao | G01J 1/0411 |
| | | | 250/353 |
| 2012/0133956 A1 | 5/2012 | Findlay et al. | |
| 2013/0050677 A1 | 2/2013 | Kwong et al. | |
| 2013/0105822 A1 | 5/2013 | Wang et al. | |
| 2015/0008329 A1* | 1/2015 | Chen | G01J 1/0242 |
| | | | 250/336.1 |
| 2015/0028378 A1 | 1/2015 | Tu et al. | |
| 2015/0208933 A1 | 7/2015 | Satomi et al. | |
| 2015/0226839 A1 | 8/2015 | Brandl et al. | |
| 2017/0086692 A1* | 3/2017 | Freschi | A61B 5/14552 |

OTHER PUBLICATIONS

International Search Report based on application No. PCT/EP2018/063342 (6 pages + 4 pages English Translation) dated Nov. 27, 2018 (for reference purpose only).

Osram Opto Semiconductors GmbH; "Light is wearable—The new SFH 7050 for Biomonitoring applications".

* cited by examiner

SENSOR AND BIOSENSOR

CROSS-REFERENCE TO RELATED APPLICATIONS

The present application is a national stage entry according to 35 U.S.C. § 371 of PCT application No.: PCT/EP2018/063342 filed on May 22, 2018; which claims priority to German Patent Application Serial No.: 10 2017 111 202.2 which was filed on May 23, 2017; both of which are incorporated herein by reference in their entirety and for all purposes.

TECHNICAL FIELD

The invention relates to a sensor and a biosensor.

BACKGROUND

Optical sensors may include a light source and a light detector, wherein light of the light source is incident on a sample, for example, an object or a body part, and is scattered and/or reflected thereon. At the same time, a part of the light can be absorbed inside the sample. A part of the reflected and/or scattered light is incident on the light detector. An intensity of the light incident on the light detector can subsequently be analyzed and therefore used to ascertain a measurement signal.

In an optical proximity sensor, for example, the light intensity of the light reflected from an object can be dependent on how far away the object is from the light source and/or the sensor. If the intensity of the reflected light exceeds a defined value, the object is thus arranged close to or at a specific distance from the sensor. A proximity of the object to the sensor can thus be determined.

In a biosensor, light of the light source can be absorbed at different strengths in a sample made of biological material above the sensor depending on biological procedures which take place within the sample. At the same time, the light of the light source is scattered in the sample and is partially incident on the light detector. An intensity change of the scattered light results in a variable signal of the light detector and can be used for analyzing biological processes.

Such sensors are to have the flattest possible structural form if they are provided for installation in mobile systems, such as for example, watches, mobile telephones, or sensor wristbands.

Such sensors have the disadvantage that in general a cover is arranged over the sensor and a part of the light originating from the light source reflects from the cover and can reach the light detector without being incident on the sample. A part of the existing light intensity is thus not used for the actual measurement, but rather worsens the measurement result as an interference signal. This is disadvantageous in particular if the sensor has a flat structural form, since then a relatively large proportion of the light originating from the light source exits at a flat angle, is reflected, and is subsequently incident on the light detector.

SUMMARY

An object of the invention is to deflect light which could be incident on the light detector originating from the light source at a flat angle in such a way that this light essentially does not arrive at the light detector.

This object is achieved by the sensor and the biosensor of the independent patent claims. Further advantageous embodiments are specified in the dependent patent claims.

A sensor includes a light source, a light detector, and a housing. The housing includes an upper side. The light detector and the light source are arranged on the upper side of the housing. A web, which includes a material which absorbs or reflects light of at least one wavelength of the light source, is arranged between the light detector and the light source. The direct path between the light source and the light detector is influenced by this web in such a way that light originating from the light source, which is emitted in the direction of the light detector, is absorbed or reflected by the web and thus cannot reach the light detector. A first cover is arranged above the light detector, which cover includes a deflection region and a plane of incidence. The plane of incidence can be arranged in parallel to the first upper side of the housing in this case. The deflection region is formed in such a way that at least 80% of the light which is incident in the deflection region on the plane of incidence of the first cover from a predetermined direction and would be incident on the light detector is deflected away from the light detector because of an optical element.

This applies in particular to light which leaves the light source at a very flat angle, but is reflected above the web by a cover and would be incident directly on the light detector.

In one embodiment, the housing includes a first cavity and a second cavity. The light detector is arranged in the first cavity. The light source is arranged in the second cavity. The web is arranged between the first cavity and the second cavity. The first cover is arranged above the first cavity.

In one embodiment, the light which is incident from the predetermined direction in the deflection region on the first cover has an angle of incidence of 80 degrees or greater. The angle of incidence in this case is the angle between a vertical line of the plane of incidence and the incident light beam. An angle of incidence of 80 degrees or greater means that light which is incident very flatly on the plane of incidence is deflected away from the detector by means of the deflection region.

In one embodiment, the deflection region is arranged between the light source and the light detector.

It can be provided that light having steeper angles of incidence, for example, at at least 70 degrees or at least 65 degrees, is also deflected away from the light detector by means of the deflection region.

In one embodiment, the first cover has a reflective coating as an optical element in the deflection region.

In one embodiment, the first cover is planar on the side facing away from the housing. On the side facing toward the housing, the first cover is embodied in the deflection region as a periodic arrangement of prisms, wherein the prisms are used as an optical element. The plane of incidence of the first cover is thus located on the side of the cover facing away from the housing.

On the side facing toward the light detector, the deflection region is embodied by means of prisms. The prisms can be embodied in such a way that at least a part of the light incident on the deflection region is reflected away from the light detector within the prisms.

In one embodiment, the prisms have a triangular cross section. A lateral surface of the prism acts in this case as a reflection side, at which light which is incident on the deflection region is reflected away from the light detector.

The triangular cross section and thus the prisms can be embodied in such a way that light which is incident at a flat angle of incidence on the deflection region is totally reflected at one side of the prism and is thus deflected nearly completely away from the detector.

In one embodiment, the first cover includes a material having an index of refraction. An angle of the triangular cross section of the prisms corresponds to at least twice the arcsine of the reciprocal value of the index of refraction. The dimensions of the prism are thus suitable for a total reflection.

In one embodiment, a second cover is arranged above the second cavity. The second cover includes a plane-parallel plate. The light source can thus be covered and therefore protected from external influences.

In one embodiment, the light detector includes a detector upper side. The deflection region extends proceeding from a first region close to the web up to a region which is defined by a vertical projection of the detector upper side on the first cover. Light which, originating from the light source, is deflected at a flat angle in the direction of the first cavity, is thus deflected away from the detector by means of the deflection region. Light which is incident at a flat angle on the first cover above the light detector is not deflected, because no deflection region is provided there, and is thus incident without direction change in the first cavity. The geometrical arrangement can be selected in this case so that the light which is incident on the first cover outside the deflection region at such a flat angle is not incident on the light detector, but rather is incident on the housing within the first cavity on the side of the light detector opposite to the light source.

In one embodiment, the deflection region covers at most half of the light detector.

In one embodiment, the deflection region is embodied as a surface in a plane of the first cover, for example, the plane of incidence. The deflection region is divided into a first region and a second region, wherein the first region adjoins the web. The second region includes a curved delimitation line, which can be arranged in the plane of the first cover. The curvature of the curved delimitation line can be concave or convex. For example, the deflection region can be curved in such a way that the deflection region has a smaller extension in a connecting plane between the light source and the light cover than in edge regions of the first cavity.

In one embodiment, the first cover includes a converging region. The converging region includes a lens structure, wherein light which is incident at an angle of incidence less than 60 degrees on the converging region of the first cover is refracted toward the light detector because of the lens structure. More steeply incident light, which more probably contains a signal to be analyzed and/or an intensity change to be analyzed, can thus be bundled toward the light detector.

In one embodiment, the converging region is embodied as a Fresnel lens. Fresnel lenses are suitable in particular, since a small focal length can be achieved with them in spite of low structural height.

In one embodiment, the sensor is a biosensor.

A biosensor includes a first light source, a second light source, a light detector, and a housing. The housing includes an upper side. The light detector and the light sources are arranged on the upper side. The first light source emits green light having a wavelength between 550 and 590 nanometers. The second light source emits infrared radiation having a wavelength greater than 850 nanometers. A web, which includes a material which absorbs or reflects light of at least one wavelength of one of the two light sources, is arranged between the light sources and the light detector. A first cover is arranged above the light detector and includes a deflection region and a plane of incidence. The deflection region is formed in such a way that at least 80% of the light which is incident from a predetermined direction on the plane of incidence of the first cover in the deflection region and would be incident on the light detector is deflected away from the light detector because of an optical element. The two mentioned light sources, which emit green light or infrared radiation, respectively, are suitable as a biosensor, in particular for measuring a heart rate by means of the green light and measuring a blood oxygen content by means of the infrared radiation. Depending on the number of the red blood cells in a blood vessel, the green light is absorbed more strongly or less strongly. More or less scattered green light is thus incident on the light detector, wherein the periodic increase and decrease of the scattered light takes place at the same frequency as the heart rate. Oxygen-rich blood has a different absorption in the range of the infrared radiation having a wavelength greater than 850 nanometers than less oxygen-rich blood. The reflected and/or scattered infrared radiation can thus be used to ascertain a blood oxygen content. The light sources can be designed in this case as light-emitting semiconductor chips, in particular as light-emitting semiconductor chips having a suitable conversion material.

In one embodiment of the biosensor, the light which is incident in the deflection region on the first cover from the predetermined direction has an angle of incidence of 80 degrees or greater. The angle of incidence in this case is the angle between a vertical line of the plane of incidence and the incident light beam. An angle of incidence of 80 degrees or greater means that light which is incident very flatly on the plane of incidence is deflected away from the detector by means of the deflection region.

In one embodiment, the biosensor includes a third light source. The third light source emits red light at a wavelength between 640 and 680 nanometers. The measurement of the blood oxygen content can thus be improved.

The further embodiments described for the sensor can also be applied for the biosensor.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the illumination apparatus. In the following description, various aspects are described with reference to the following drawings, in which.

DETAILED DESCRIPTION

Figure 1:
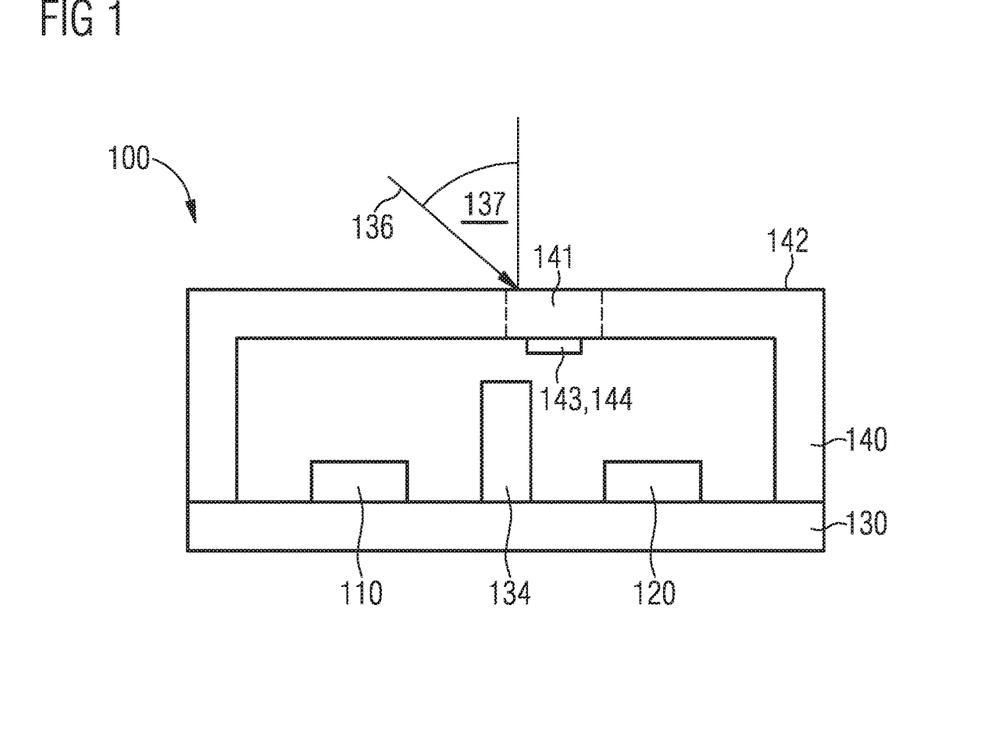
FIG. 1 shows a cross section through a sensor.

FIG. 1 shows a sensor 100 having a light source 110 and a light detector 120. The sensor 100 furthermore includes a housing 130. The light source 110 and the light detector 120 are arranged above an upper side 133 of the housing 130. A web 134 is arranged between the light source 110 and the light detector 120, wherein the web 134 includes a material which absorbs or reflects light of at least one wavelength of the light source 110. The web 134 may consist of the same material as the housing 130 and may be part of the housing 130 in this case. It is also possible that the web 134 is placed on the housing 130. The direct path from the light source 110 to the light detector 120 is blocked by the web 134. A first cover 140 is arranged above the light detector 120. The first cover 140 includes a deflection region 141 and a plane of incidence 142. The deflection region 141 is embodied as a reflective coating 144 on a side of the first cover 140 facing toward the housing 130. The reflective coating 144 of the deflection region 141 is used in this case as an optical element 143 and is embodied in this case in such a way that at least 80% of the light which is incident in the deflection region on the plane of incidence 142 of the first cover 140 is deflected away from the light detector 120. The deflection region 141 is arranged in this case on a side of the first cover 140 facing toward the web 134. Light which is incident from a predetermined direction 136 at a relatively flat angle of incidence 137 on the deflection region 141 of the first cover 140 and would reach the light detector 120 in a direct line is deflected away from the light detector 120 by the reflective coating 144 of the deflection region 141. The first cover 140 may include a glass or a transparent plastic.

Alternatively to the embodiment shown in FIG. 1, the reflective coating 144 can also be arranged on the side of the first cover 140 facing away from the housing.

Figure 2:
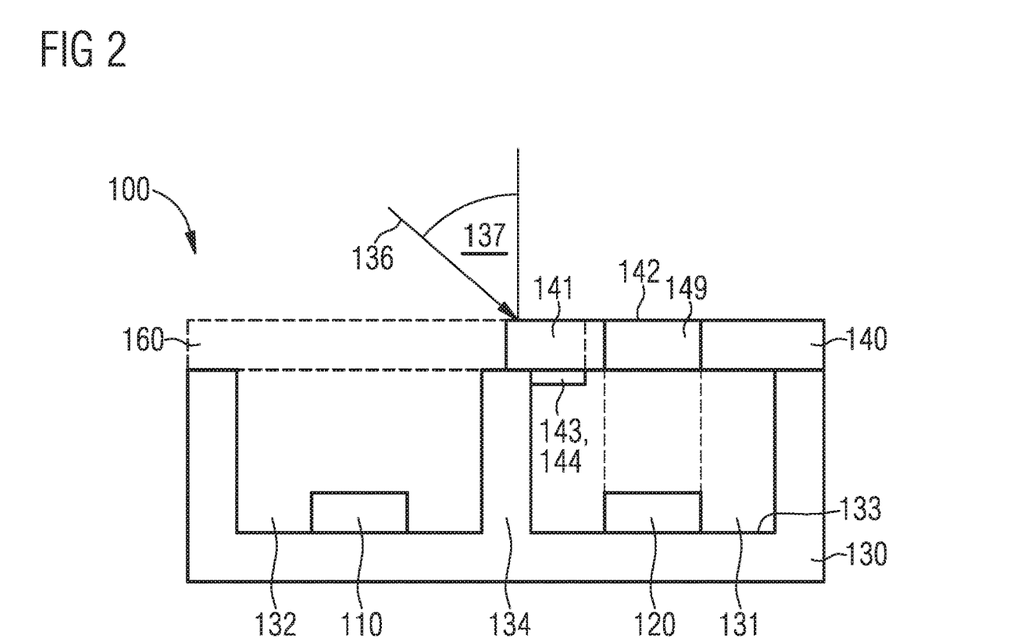
FIG. 2 shows a cross section through a sensor.

FIG. 2 shows a sensor 100 having a light source 110 and a light detector 120. The sensor 100 furthermore includes a housing 130. Proceeding from a first upper side 133 of the housing 130, the housing 130 includes a first cavity 131 and a second cavity 132. A web 134 is arranged between the first cavity 131 and the second cavity 132, wherein the web 134 includes a material which absorbs or reflects light of at least one wavelength of the light source 110. The web 134 consists in this case of the same material as the housing 130 and is part of the housing 130. It is also possible that the web 134 is inserted into the housing 130 and thus separates the first cavity 131 from the second cavity 132. The direct path from the light source 110 to the light detector 120 is blocked by the web 134. A first cover 140 is arranged above the first cavity 131. The first cover 140 includes a deflection region 141 and a plane of incidence 142. The deflection region 141 is embodied as a reflective coating 144 on a side of the first cover 140 facing toward the housing 130. The reflective coating 144 of the deflection region 141 is used in this case as an optical element 143 and is embodied in this case in such a way that at least 80% of the light which is incident in the deflection region on the plane of incidence 142 of the first cover 140 is deflected away from the light detector 120. The deflection region 141 is arranged in this case on a side of the first cover 140 facing toward the web 134. Light which is incident from a predetermined direction 136 at a relatively flat angle of incidence 137 on the deflection region 141 of the first cover 140 and would reach the light detector 120 in a direct line is deflected away from the light detector 120 by the reflective coating 144 of the deflection region 141. The first cover 140 may include a glass or a transparent plastic. A region 149 represents the vertical projection of the detector upper side 121 on the first cover 140.

Alternatively to the embodiment shown in FIG. 2, the reflective coating 144 can also be arranged on the side of the first cover 140 facing away from the housing.

In one embodiment, the light which is incident from the predetermined direction 136 in the deflection region 141 on the first cover has an angle of incidence 137 of 80 degrees or greater. The angle of incidence 137 is in this case an angle between a vertical line to the plane of incidence 142 and the incident light. The deflection region 141 is arranged in this case between the light source 110 and the light detector 120, as shown in FIG. 2.

The light source 110 may in this case include a light-emitting semiconductor chip. This chip can be provided with a conversion phosphor. The light detector 120 may include a photodiode. The housing 130 can consist of a plastic or of metal, wherein terminal elements (not shown in the figures) can be provided for the light source 110 and the light detector 120.

Figure 3:
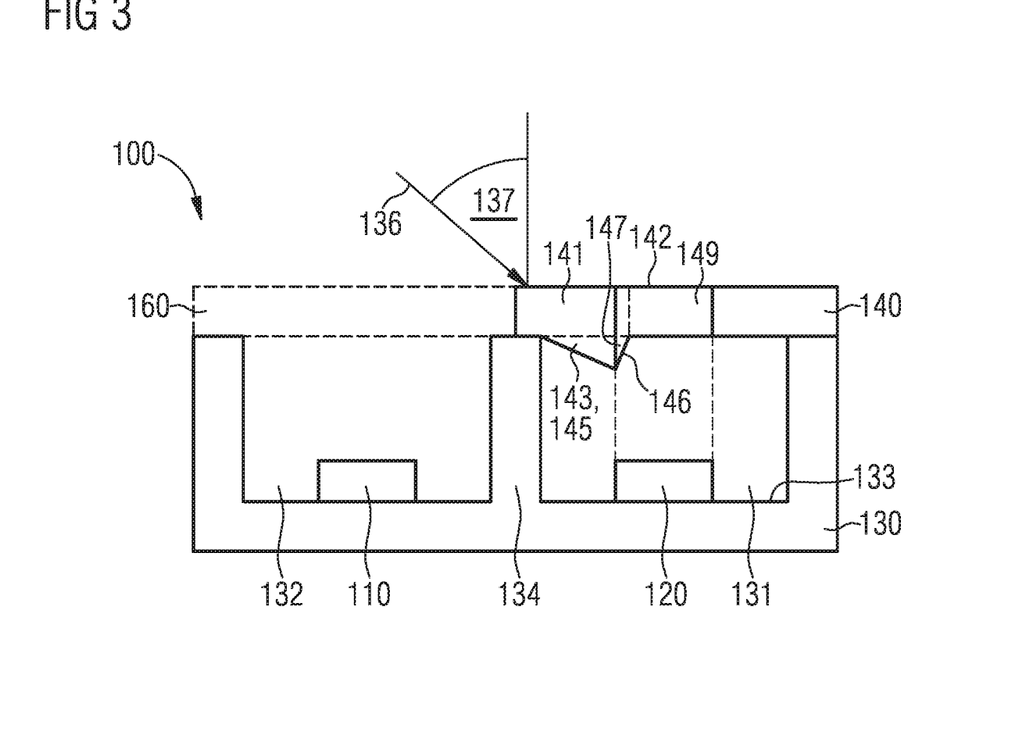
FIG. 3 shows a further cross section through a sensor.

FIG. 3 shows a further embodiment of a sensor 100, which essentially corresponds to the sensor 100 of FIG. 2. Only the optical element 143 in the deflection region 141 of the first cover 140 is embodied differently in the sensor 100 of FIG. 3. A prismatic structure 145, which is triangular in cross section and is used as an optical element 143, is arranged on a side of the first cover 140 facing toward the housing. The prismatic structure 145 includes a reflection side 146, which is arranged on the side of the prismatic structure 145 facing away from the web 134. An angle 147 between the lower side of the first cover 140 and the reflection side 146 is sufficiently large that light which is incident from a predetermined direction 136 at an angle of incidence 137 on the plane of incidence 142 of the first cover 140, and which would be incident on the light detector 120 without the deflection region 141, is incident at a total reflection angle on the reflection side 146 because of the light refraction inside the first cover 140 having the prismatic structure 145. The incident light is thus totally reflected at the reflection side 146 and thus deflected away from the light detector 120. A region 149 represents the vertical projection of the detector upper side 121 on the first cover 140.

Figure 4:
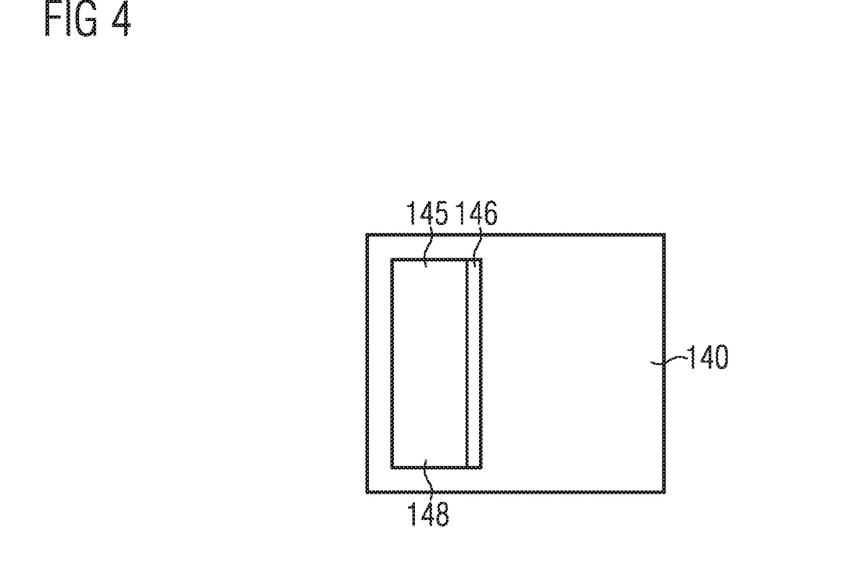
FIG. 4 shows a top view of a first cover.

FIG. 4 shows a top view of the lower side of the first cover 140 of FIG. 3. The prismatic structure 145 is arranged on the lower side. In order that the light incident from the predetermined direction 136 is totally reflected on the reflection side 146, the reflection side 146 has to be steeper than a further side 148 of the prismatic structure 145.

In one embodiment, the light which is incident from the predetermined direction 136 in the deflection region 141 on the first cover has an angle of incidence 137 of 80 degrees or greater. The angle of incidence 137 is in this case an angle between a vertical line to the plane of incidence 142 and the incident light. The deflection region 141 is arranged in this case between the light source 110 and the light detector 120, as shown in FIG. 3.

The angle 147 can also be selected so that light having a steeper angle of incidence 137, for example, 70 or 65 degrees in relation to the vertical line to the plane of incidence 142, is deflected away from the light detector 120 because of the total reflection at the reflection side 146.

Figure 5:
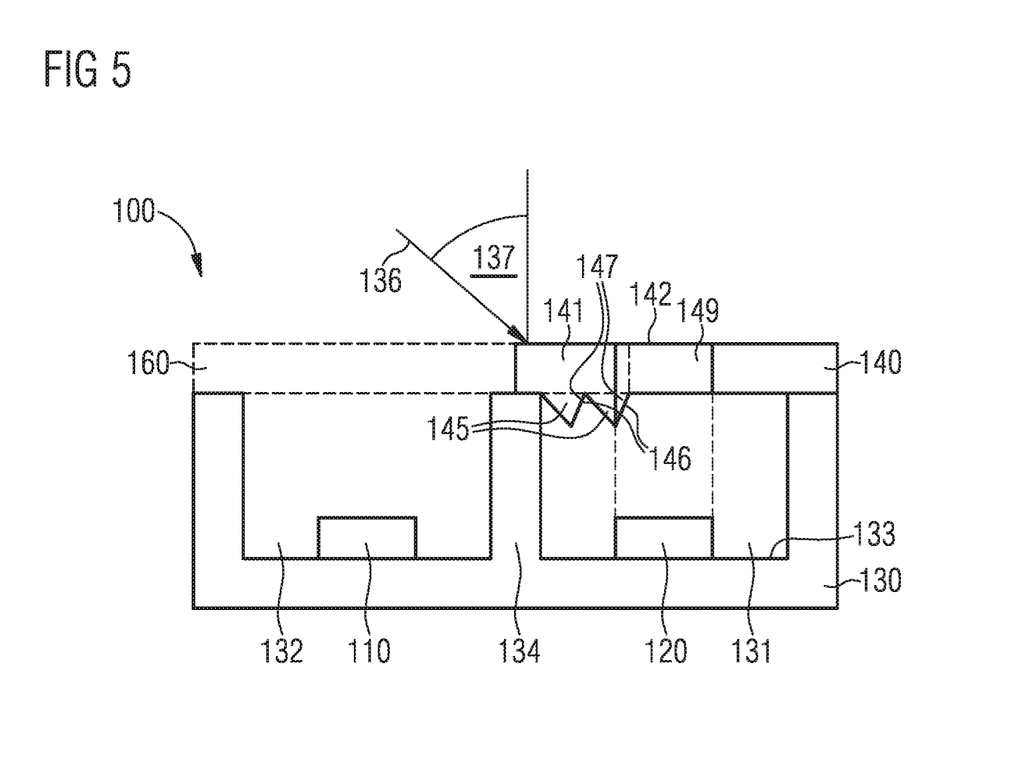
FIG. 5 shows a further cross section through a sensor having a deflection region consisting of multiple prismatic structures.

FIG. 5 shows a further cross section through a sensor 100, which essentially corresponds to the sensor 100 of FIG. 3. In the deflection region 141, the sensor 100 of FIG. 5 includes multiple prismatic structures 145, which are identical to one another. The prismatic structures 145 are arranged adjacent to one another and adjoining one another and each include a reflection side 146 and an angle 147 similar to FIG. 3. A structural height of the first cover 140 can be reduced because the deflection region includes an arrangement of multiple prismatic structures 145.

The first cover is thus embodied in the deflection region 141 on the side facing toward the housing 130 as a periodic arrangement of prisms 145. A region 149 represents the vertical projection of the detector upper side 121 on the first cover 140.

Figure 6:
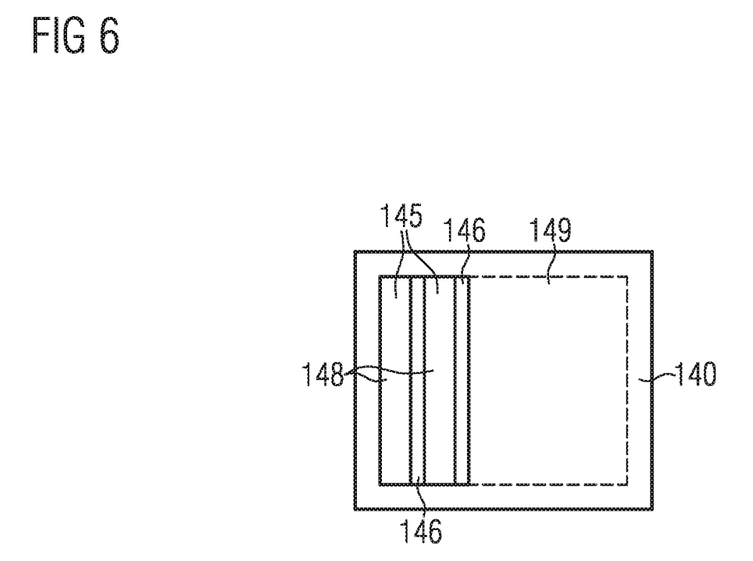
FIG. 6 shows a top view of a first cover having multiple prismatic structures.

FIG. 6 shows a top view of the lower side of the first cover 140 of FIG. 5. Two prismatic structures 145 are arranged on the lower side. In order that the light incident from the predetermined direction 136 is totally reflected at the reflection side 146, the reflection side 146 has to be steeper than a further side 148 of the prismatic structures 145. The prismatic structures 145 are arranged in this case so that the reflection side 146 of one of the two prismatic structures 145 is facing toward the further side 148 of the other of the two prismatic structures 145.

The prismatic structures 145 of the first cover 140 of FIGS. 3 to 6 can alternatively also be arranged on the side of the first cover 140 facing away from the light detector 120.

An optional second cover 160, which is arranged above the second cavity 132 and is embodied as a plane-parallel plate, is shown by dashed lines in FIGS. 2, 3, and 5. The second cover 160 may include a glass or a plastic. The first cover 140 and the second cover 160 can also be embodied in one piece in this case.

In addition to the prisms 145 having triangular cross section and reflection side 146, the deflection regions 141 of FIGS. 3 to 6 can also be embodied having prisms of a different base, for example, having a quadrilateral or pentagonal cross section. More than two prismatic structures 145 can also be provided.

In one embodiment, the first cover 140 and the prismatic structure 145 include a material having a first index of refraction. The angle 147 between the reflection side 146 and the lower side of the cover 140 corresponds in this case to at least twice the arcsine of the reciprocal value of the index of refraction of the material. Light which is incident on the plane of incidence 142 in the region of the deflection region 141 at a flat angle of incidence 137 is thus totally reflected at the reflection side 146.

A region 149 represents the vertical projection of the detector upper side 121 on the first cover 140.

Figure 7:
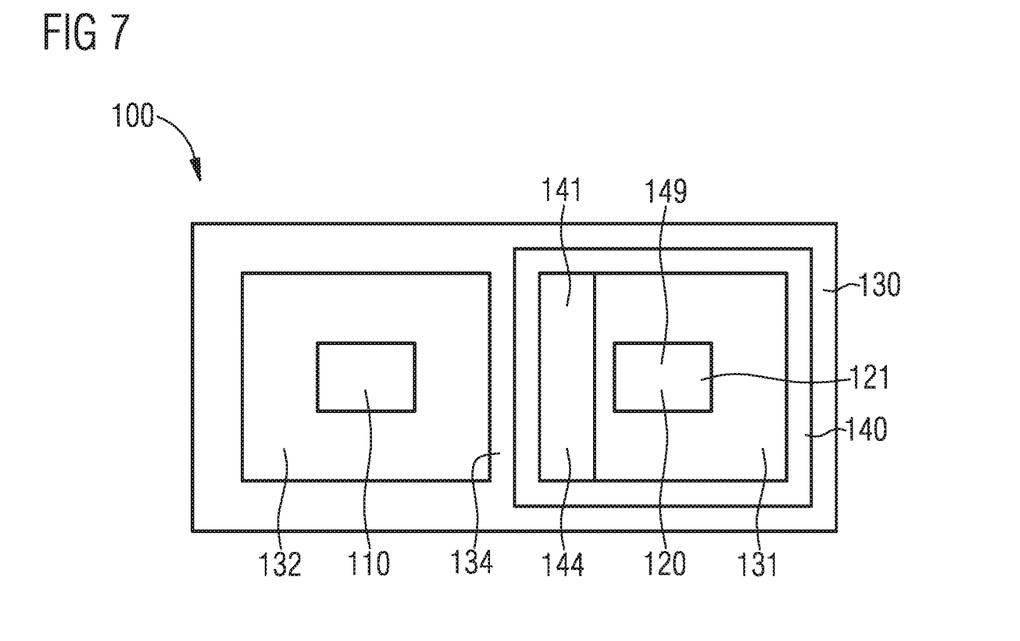
FIG. 7 shows a top view of a sensor.

FIG. 7 shows a top view of a sensor 100, which can essentially correspond to one of the sensors 100 of FIGS. 2 to 6. The housing 130 includes a first cavity 131 and a second cavity 132, wherein a light detector 120 is arranged in the first cavity and a light source 110 is arranged in the second cavity. A web 134 is arranged between the cavities 131, 132. A first cover 140 having a deflection region 141 is arranged above the first cavity 131. The deflection region 141 adjoins the web 134 in this case. The deflection region 141 is embodied as sufficiently narrow in the direction of the light detector 120 that the deflection region 141 does not cover the light detector 120. This essentially corresponds to the illustration of the sensor 100 of FIG. 2, in which the reflective coating 144 does not cover the light detector 120. The deflection region 141 can also be the prismatic structures of FIGS. 3 to 6, however. A region 149 represents the vertical projection of the detector upper side 121 on the first cover 140. The region 148 is thus arranged outside the deflection region 141.

It can be provided that the deflection region 141, as illustrated in FIGS. 3 and 5, partially covers the light detector 120. The deflection region 141 and the region 148 thus overlap.

In one embodiment, the deflection region 141 covers at most half of the light detector 120.

Figure 8:
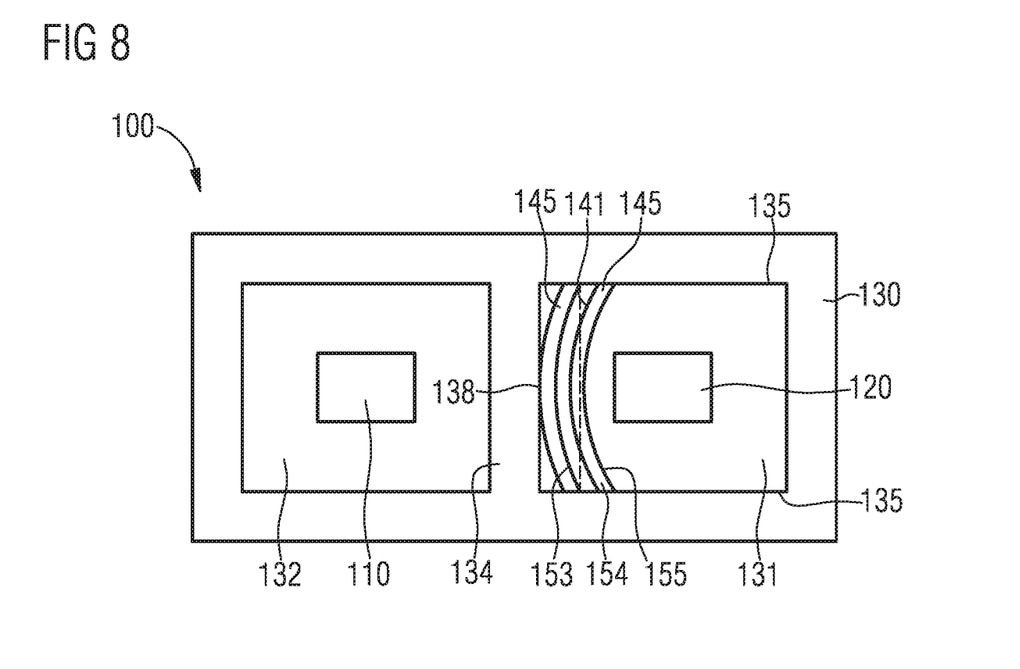
FIG. 8 shows a top view of a sensor having curved deflection region.

FIG. 8 shows a top view of a sensor 100, which essentially corresponds to the sensor 100 of FIG. 6. The deflection region 141 is formed as a periodic arrangement of prismatic structures 145. The prismatic structures 145 are curved in a plane of the first cover 140 in this case in such a way that the prismatic structures 145 adjoin the web 134 in a first region 153 in a middle 138 of the web 134 and are curved away from the web 134 outside the middle 138 of the web 134. In a second region 154, which is opposite to the web 134, the deflection region 141 includes a curved delimitation line 155. Alternatively, the prismatic structures 145 can be arranged spaced apart from the web 134 in a middle 138 of the web 134. In edge regions 135 of the first cavity 131, the prismatic structures 145 of the deflection region 141 thus do not adjoin the web 134. Laterally incident light can thus also be deflected away from the light detector 120.

Alternatively, the cover of FIG. 8 may also only include one prismatic structure 145 similarly to FIG. 3 or one reflective coating similarly to FIG. 2, which is also curved as shown in FIG. 8. Such a curvature is concave.

Furthermore, it can be provided that the deflection region 141 has its greatest extension adjoining the middle 138 of the web 134 and has a smaller extension in the edge regions 135. The curvature of the deflection region 141 is thus convex. The curved delimitation line 155 can thus be curved concave or convex.

Figure 9:
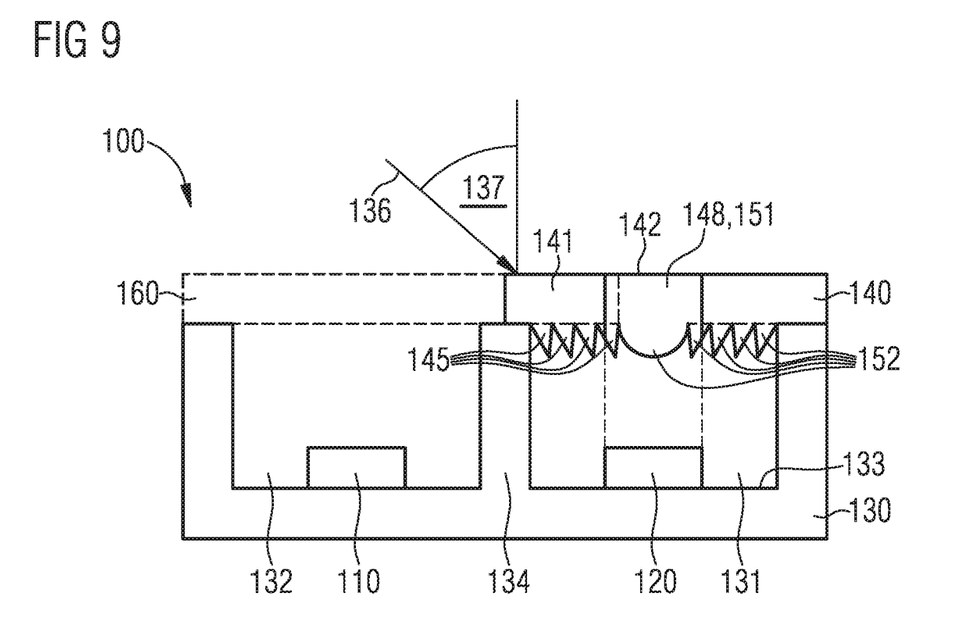
FIG. 9 shows a cross section through a sensor, in which the first cover includes a deflection region and a converging region.

FIG. 9 shows a cross section through a sensor 100, in which the deflection region 141 is constructed from a periodic arrangement of prisms 145 similarly to FIG. 5. The deflection region 141 partially covers the light detector 120 in the region 149 in this case, which in turn is a vertical projection of the detector surface 121 on the first cover 140. Adjoining the deflection region 141, the first cover 140 includes a converging region 151. The converging region 151 includes a lens structure, wherein light which is incident at an angle of incidence less than 60 degrees on the converging region 151 of the first cover 140 is refracted toward the light detector 120 because of the lens structure. The lens structure is embodied in this case having Fresnel lens elements 152. However, another design of the lens structure of the converging region 151 is also conceivable.

Figure 10:
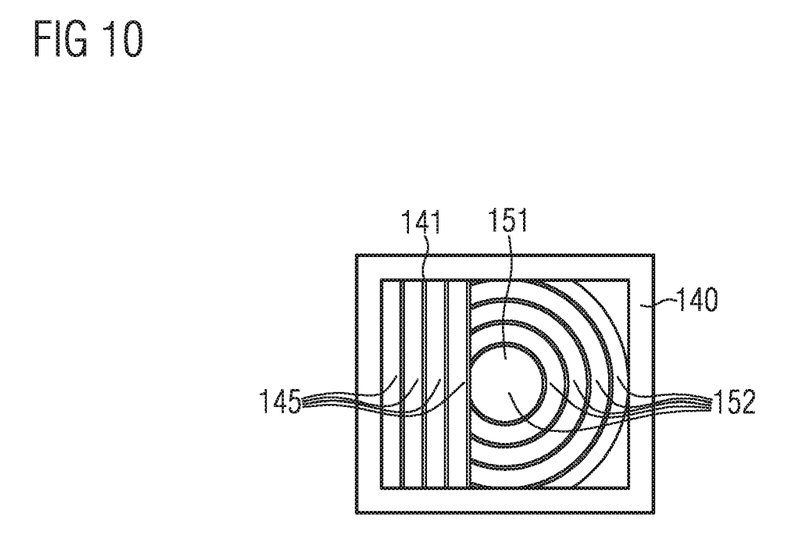
FIG. 10 shows a top view of a first cover having deflection region and converging region.

FIG. 10 shows a top view of the lower side of the first cover of FIG. 9. Four prismatic structures 145, which are arranged parallel to the web 134, form the deflection region 141 and are constructed similarly to FIGS. 3 to 6. Alternatively, the prismatic structures 145 may also include a convex or concave curvature similar to FIG. 8. The first cover 140 includes a converging region 151 adjoining the deflection region 141. The converging region 151 includes a lens structure which is embodied having Fresnel lens elements 152. A middle of the converging region 151 is arranged above a middle of the light detector 120.

The first cover 140 having the deflection region as prismatic structures 145 and also optionally the converging region 151 having the Fresnel lens elements can be provided in this case as a molded body, for example, as an injection-molded or cast body.

The embodiments according to FIGS. 1 to 10 may also include more than one light source 110 in the second cavity 132. The light sources 110 can then have different or identical wavelengths.

Figure 11:
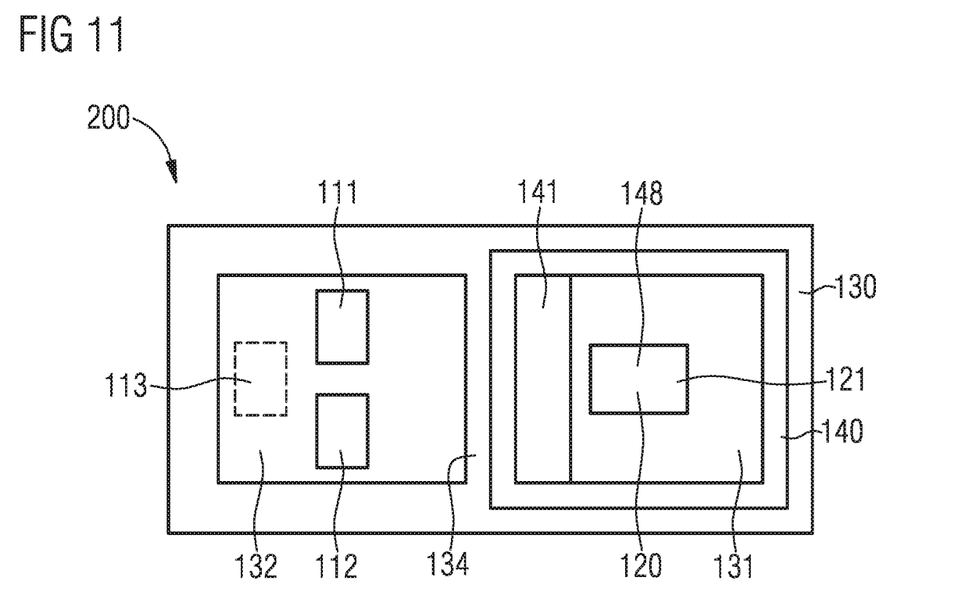
FIG. 11 shows a top view of a biosensor.

FIG. 11 shows a top view of a biosensor 200, which includes a first light source 111 and a second light source 112, a light detector 120, and a housing 130. The housing 130 includes a first upper side 133 similarly to the housing 130 of FIG. 2. Proceeding from the first upper side 133, the housing 130 includes a first cavity 131 and a second cavity 132. A web 134 is arranged between the first cavity 131 and the second cavity 132 similarly to FIG. 2 and consists of a material which absorbs or reflects light of at least one of the light sources 111, 112. A first cover 140 having a deflection region 141 is arranged above the first cavity 131. The first light source 111 emits green light of a wavelength between 550 and 590 nanometers in this case, while the second light source 112 emits infrared radiation having a wavelength greater than 850 nanometers. The deflection region 141 is formed in such a manner that at least 80% of the light which is incident on the deflection region 141 of the first cover 140 from a predetermined direction 136 at a relatively flat angle of incidence 137 similarly to FIGS. 2, 3, and 5 and would reach the light detector 120 in a direct line is deflected away by the deflection region 141 from the light detector 120. The first cover 140 may include a glass or a transparent plastic.

The first light source 111 and the second light source 112 may each include a light-emitting semiconductor chip in this case. Furthermore, the first light source 111 and the second light source 112 may include a conversion phosphor.

A third light source 113 is also arranged in the second cavity 132 in FIG. 11, but shown by dashed lines. This third light source emits red light having a wavelength between 640 and 680 nanometers. The third light source 113 may also include a light-emitting semiconductor chip and may include a conversion phosphor.

The biosensor 200 is thus capable of ascertaining a heart rate by means of the first light source 111 by applying the biosensor 200 to a tissue having blood vessels and of ascertaining a blood oxygen content by means of the second 112 and possibly the third light source 113. Scattered light which is incident on the first cover 140 at a flat angle of incidence 137 is deflected away from the light detector 120 by the deflection region 141.

Instead of the light detector 120, multiple light detectors each having a filter for the wavelengths originating from the light sources 111, 112, 113 can also be arranged in the first cavity 131.

The further designs of the first cover 140 and the optional second cover 160, as described in FIGS. 1 to 10, can also be arranged on the biosensor 200 of FIG. 11. The biosensor 200 can thus be designed according to the exemplary embodiments of FIGS. 1 to 10.

Although the invention was illustrated and described in greater detail by the preferred embodiments, the invention is not restricted by the disclosed examples and other variations can be derived therefrom by a person skilled in the art, without leaving the scope of protection of the invention.

LIST OF REFERENCE SIGNS 100 sensor
110 light source
111 first light source
112 second light source
113 third light source
120 light detector
121 detector upper side
130 housing
131 first cavity
132 second cavity
133 upper side
134 web
135 edge regions
136 predetermined direction
137 angle of incidence
138 middle
140 first cover
141 deflection region
142 plane of incidence
143 optical element
144 reflective coating
145 prismatic structure
146 reflection side
147 angle
148 further side
149 region
151 converging region
152 Fresnel lens element
153 first region
154 second region
155 curved delimitation line
160 second cover
200 biosensor

The invention claimed is:

1. A sensor, comprising:
at least one light source,
a light detector, and
a housing comprising an upper side, wherein the light detector and the light source are arranged on the upper side,
a web arranged between the light source and the light detector, wherein the web comprises a material which absorbs or reflects light of at least one wavelength of the light source,
an optical element comprising one or more prismatic structures,
a first cover arranged above the light detector, wherein the first cover comprises a deflection region and a plane of incidence, wherein the deflection region is formed in such a manner that at least 80% of the light, which is incident from a predetermined direction in the deflection region on the plane of incidence of the first cover and would be incident on the light detector, is deflected away from the light detector because of the optical element, wherein the optical element is arranged on a lower side of the first cover facing the housing.

2. The sensor as claimed in claim 1, wherein:
the light which is incident from the predetermined direction in the deflection region on the first cover has an angle of incidence of 80 degrees or greater,
the angle of incidence is an angle between a vertical line to the plane of incidence and the incident light, and
the deflection region is arranged between the light source and the light detector.

3. The sensor as claimed in claim 1, wherein:
the first cover is planar on the side facing away from the housing, and
the one or more prismatic structures comprises a plurality of prismatic structures embodied as a periodic arrangement of prisms.

4. The sensor as claimed in claim 3, wherein the prisms have a triangular cross section.

5. The sensor as claimed in claim 4, wherein:
the first cover comprises a material having an index of refraction, and
an angle of the triangular cross section of the prisms corresponds to at least twice the arcsine of the reciprocal value of the index of refraction.

6. The sensor as claimed in claim 1, wherein:
the light detector comprises a detector upper side,
the deflection region extends proceeding from a region close to the web up to a region, and
the region is defined by a vertical projection of the detector upper side on the first cover.

7. The sensor as claimed in claim 6, wherein the deflection region covers at most half of the light detector.

8. The sensor as claimed in claim 1, wherein:
the deflection region is embodied as an area in a plane of the first cover,
the deflection region is divided into a first region and a second region,
the first region adjoins the web, and
the second region comprises a curved delimitation line, wherein the curvature of the curved delimitation line is concave or convex.

9. The sensor as claimed in claim 1, wherein:
the first cover comprises a converging region,
the converging region comprises a lens structure, and
light which is incident on the converging region of the first cover at an angle of incidence less than 60 degrees is refracted toward the light detector because of the lens structure.

10. The sensor as claimed in claim 9, wherein the converging region is embodied as a portion of a Fresnel lens.

11. The sensor as claimed in claim 1, wherein the sensor is designed as a biosensor.

12. The sensor as claimed in claim 1, wherein:
an angle between the lower side of the first cover and a reflection side of the prismatic structure is sufficiently large that light which is incident from a predetermined direction at an angle of incidence on the plane of incidence of the first cover, and
the light would be incident on the light detector without the deflection region, is incident at a total reflection angle on the reflection side because of the light refraction within the first cover having the prismatic structure.

13. The sensor as claimed in claim 1, wherein the first cover fully extends over the light detector.

14. The sensor as claimed in claim 1, wherein the first cover comprises a transparent material.

15. A biosensor device comprising:
a first light source and a second light source; wherein the first light source emits green light at a wavelength from 550 to 590 nanometers and the second light source emits infrared radiation having a wavelength greater than 850 nanometers;
a light detector; and
a housing comprising an upper side, wherein the light detector and the light sources are arranged on the upper side;
a web arranged between the light sources and the light detector, wherein the web comprises a material which absorbs or reflects light of at least one wavelength of one of the two light sources;
an optical element;
a first cover arranged above the light detector, wherein the first cover comprises a deflection region and a plane of incidence and where the deflection region is formed in such a manner that at least 80% of the light, which is incident from a predetermined direction in the deflection region on the plane of incidence of the first cover and would be incident on the light detector, is deflected away from the light detector because of the optical element wherein the optical element is arranged on a lower side of the first cover facing the housing.

16. The biosensor as claimed in claim 15, wherein:
the light which is incident from the predetermined direction in the deflection region on the first cover has an angle of incidence of 80 degrees or greater, and
the angle of incidence is an angle between a vertical line to the plane of incidence and the incident light, and wherein the deflection region is arranged between the light sources and the light detector.

17. The biosensor as claimed in claim 15,
further comprising a third light source, and
wherein the third light source emits red light having a wavelength between 640 and 680 nanometers.

18. The biosensor as claimed in claim 15, wherein the first cover fully extends over the light detector.

19. The biosensor as claimed in claim 15, wherein the first cover comprises a transparent material.

* * * * *